United States Patent
Bienvenu et al.

(10) Patent No.: US 12,268,602 B2
(45) Date of Patent: Apr. 8, 2025

(54) TELESCOPING CAPSULE ASSEMBLY FOR TRANSCATHETER VALVE REPAIR AND METHODS

(71) Applicant: Medtronic, Inc., Minneapolis, MN (US)

(72) Inventors: Ryan J. Bienvenu, Santa Rosa, CA (US); Grant A. Menon, Santa Rosa, CA (US); Fatemeh Fatemi Far, Santa Rosa, CA (US); Sabrina Hua, San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 251 days.

(21) Appl. No.: 17/698,177

(22) Filed: Mar. 18, 2022

(65) Prior Publication Data
US 2022/0346951 A1 Nov. 3, 2022

Related U.S. Application Data

(60) Provisional application No. 63/183,107, filed on May 3, 2021.

(51) Int. Cl.
*A61F 2/24* (2006.01)
*A61F 2/48* (2006.01)

(52) U.S. Cl.
CPC .......... *A61F 2/2436* (2013.01); *A61F 2/2418* (2013.01); *A61F 2/484* (2021.08)

(58) Field of Classification Search
CPC ....... A61F 2/2436; A61F 2/484; A61F 2/2418
See application file for complete search history.

(56) References Cited

U.S. PATENT DOCUMENTS

| 10,786,352 B2 | 9/2020 | Francis et al. |
| 2018/0126121 A1 | 5/2018 | Mauch |
| 2018/0344454 A1* | 12/2018 | Mauch ............... A61F 2/844 |
| 2020/0069422 A1 | 3/2020 | Essinger et al. |
| 2020/0205972 A1 | 7/2020 | Nyuli et al. |
| 2020/0261218 A1 | 8/2020 | Mauch et al. |

FOREIGN PATENT DOCUMENTS

WO 2014/121280 A2 8/2014

OTHER PUBLICATIONS

Extended European Search Report, EP Application No. 22171087.4, dated Sep. 7, 2022.

* cited by examiner

*Primary Examiner* — Suba Ganesan
(74) *Attorney, Agent, or Firm* — Medler Ferro Woodhouse & Mills PLLC

(57) ABSTRACT

Aspects of the disclosure provide a cardiac implant delivery device including catheter having a distal end and a telescoping capsule assembly secured to the distal end. The capsule assembly can include a distal capsule and a proximal capsule. Other embodiments include additional capsules positioned between the proximal and distal capsules. The capsule assembly has a loaded arrangement and a deployed arrangement. As the capsule assembly transitions from the loaded arrangement fully covering the implant to the deployed arrangement, the proximal capsule and any intermediate capsules move distally in the direction of the distal capsule to unsheathe the implant. In various embodiments, the cardiac implant is a prosthetic heart valve. Methods of delivering a cardiac implant are also disclosed. Various methods include methods of delivering a replacement tricuspid heart valve.

17 Claims, 12 Drawing Sheets

TELESCOPING CAPSULE ASSEMBLY FOR TRANSCATHETER VALVE REPAIR AND METHODS

CROSS-REFERENCE TO RELATED APPLICATIONS

This Non-Provisional patent application claims the benefit of the filing date of U.S. Provisional Patent Application Ser. No. 63/183,107, filed May 3, 2021, entitled "TELESCOPING CAPSULE ASSEMBLY FOR TRANSCATHETER VALVE REPAIR AND METHODS," the entire teachings of which are incorporated herein by reference.

FIELD

The present technology is generally related to delivery devices and methods for transcatheter delivery and deployment of a prosthesis to a heart valve.

BACKGROUND

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of a prosthetic heart valve or prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place.

The present disclosure addresses problems and limitations associated with the related art.

SUMMARY

The techniques of this disclosure generally relate to delivery devices and methods for transcatheter delivery and deployment of a prosthesis, such as a prosthetic heart valve, to a defective heart valve. Aspects of the disclosure include a telescoping capsule to compressively retain the prosthesis during delivery. Aspects of the disclosure are particularly beneficial for transcatheter tricuspid valve repair as various delivery devices are configured to reduce the depth in which the device needs to be inserted into the right ventricle during delivery of the prosthesis. Access to a tricuspid valve can be challenging in that existing implanted devices may be in the anatomy, reducing the space available for the delivery device. In addition, visualization of the delivery system and implant may be challenging as metallic capsules can cause artifacts due to density. Further, chordae and papillary muscles serve as obstacles for delivery and the right ventricle is generally shorter than the left ventricle. All of these considerations result in a general desire for a system capable of delivering an implant to a tricuspid valve while reducing a length the delivery device extends into the right ventricle and past the valve annulus.

In one aspect, the present disclosure provides a cardiac implant delivery device including a catheter assembly including a catheter having a distal end. The delivery device further includes a capsule assembly secured to the distal end. The capsule assembly configured to sheathe the cardiac implant. The capsule assembly further including a distal capsule and a proximal capsule, the distal capsule positioned distally with respect to the proximal capsule. The capsule assembly also includes a loaded arrangement and a deployed arrangement. The proximal capsule moves distally as the capsule assembly transitions from the loaded arrangement to the deployed arrangement.

In another aspect, the disclosure provides methods of delivering an implant to a heart valve. Such methods can include providing a delivery device including a catheter assembly with a catheter having a distal end and a capsule assembly secured to the distal end. The capsule assembly is configured to sheathe the implant. The capsule assembly includes a distal capsule and a proximal capsule. The distal capsule is positioned distally with respect to the proximal capsule in a loaded arrangement and the implant is secured over the distal end and within the capsule assembly. Methods can further include directing the delivery device to the heart valve and transitioning the capsule assembly from the loaded arrangement to an arrangement in which the proximal capsule is advanced distally over the distal capsule and a proximal end of the implant is at least partly unsheathed.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

As referred to herein, implants, prostheses, stented prosthetic heart valves or "prosthetic valves" useful with the various systems, devices and methods of the present disclosure may assume a wide variety of configurations. Stented prosthetic heart valves can include, for example, a bioprosthetic heart valve having tissue leaflets or a synthetic heart valve having polymeric, metallic or tissue-engineered leaflets, and can be specifically configured for replacing valves of the human heart. The prosthetic valves and stented prostheses of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having an uncompressed, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol). The stent frame can be laser-cut from a single piece of material, or can be assembled from a number of discrete components.

Figure 1A:
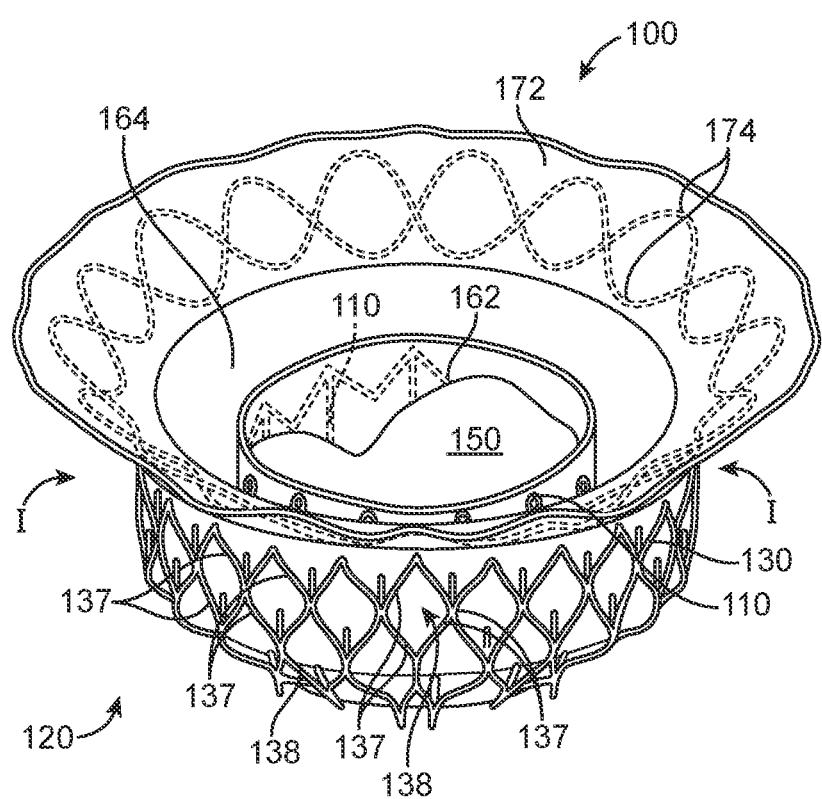
FIG. 1A is a top isometric view of a prosthetic heart valve in an expanded arrangement.
Figure 1B:
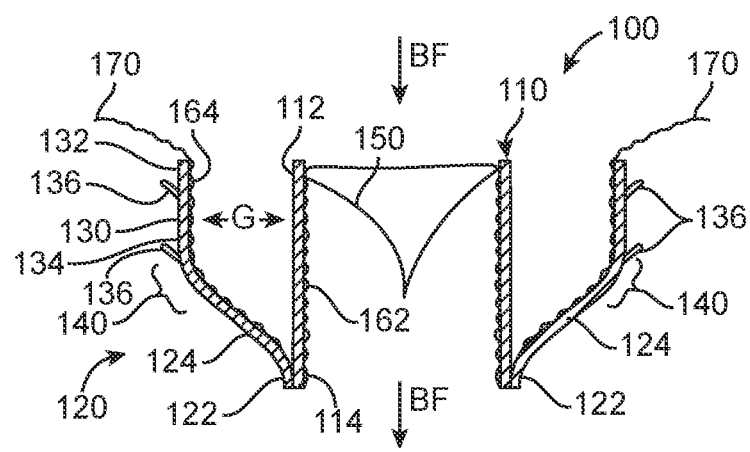
FIG. 1B is a cross-sectional side view of the prosthetic heart valve of FIG. 1A.
Figure 1C:
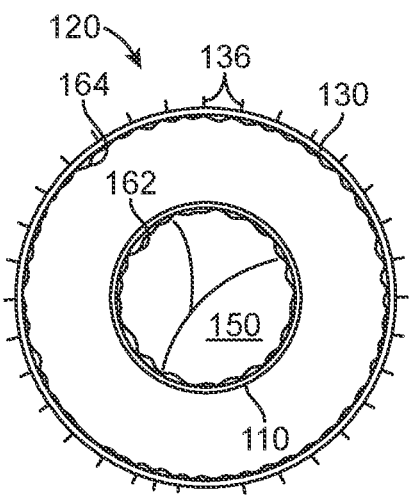
FIG. 1C is a top view schematically illustrating the prosthetic heart valve of FIGS. 1A-1B.

One non-limiting example of a stented prosthesis or implant 100 suitable for use with systems and devices of the disclosure is illustrated in FIGS. 1A-1C. In this example, the implant is a prosthetic heart valve 100 includes a valve support 110, an anchoring member 120 attached to the valve support 110, and a prosthetic valve assembly 150 within the valve support 110. Referring in particular to FIG. 1B, the valve support 110 has an inflow region 112 and an outflow region 114. The prosthetic valve assembly 150 is arranged within the valve support 110 to allow blood to flow from the inflow region 112 through the outflow region 114 (arrows BF), but prevent blood from flowing in a direction from the outflow region 114 through the inflow region 112.

The anchoring member 120 includes a base 122 attached to the outflow region 114 of the valve support 110 and a plurality of arms 124 projecting laterally outward from the base 122. The anchoring member 120 also includes a fixation structure 130 extending from the arms 124. The fixation structure 130 can include a first portion 132 and a second portion 134. The first portion 132 of the fixation structure 130, for example, can be an upstream region of the fixation structure 130 that, in a deployed configuration as shown in FIG. 1B, is spaced laterally outward apart from the inflow region 112 of the valve support 110 by a gap G. The second portion 134 of the fixation structure 130 can be a downstream-most portion of the fixation structure 130. The fixation structure 130 can be a cylindrical ring (e.g., straight cylinder or conical), and the outer surface of the fixation structure 130 can define an annular engagement surface configured to press outwardly against the native heart valve annulus. The fixation structure 130 can further include a plurality of fixation elements 136 that project radially outward and are inclined toward an upstream direction. The fixation elements 136, for example, can be barbs, hooks, or other elements that are inclined only in the upstream direction (e.g., a direction extending away from the downstream portion of the implant 100).

The anchoring member 120 has a smooth bend 140 between the arms 124 and the fixation structure 130. For example, the second portion 134 of the fixation structure 130 extends from the arms 124 at the smooth bend 140. The arms 124 and the fixation structure 130 can be formed integrally from a continuous strut or support element such that the smooth bend 140 is a bent portion of the continuous strut. In other examples, the smooth bend 140 can be a separate component with respect to either the arms 124 or the fixation structure 130. For example, the smooth bend 140 can be attached to the arms 124 and/or the fixation structure 130 using a weld, adhesive or other technique that forms a smooth connection. The smooth bend 140 is configured such that the implant 100 can be recaptured in a capsule or other container after the implant 100 has been at least partially deployed.

The implant 100 can further include a first sealing member 162 on the valve support 110 and a second sealing member 164 on the anchoring member 120. The first and second sealing members 162, 164 can be made from a flexible material, such as a polymeric material. The first sealing member 162 can cover the interior and/or exterior surfaces of the valve support 110. The first sealing member 162 is attached to the interior surface of the valve support 110, and the prosthetic valve assembly 150 is attached to the first sealing member 162 and commissure portions of the valve support 110. The second sealing member 164 is attached to the inner surface of the anchoring member 120. As a result, the outer annular engagement surface of the fixation structure 130 is not covered by the second sealing member 164 so that the outer annular engagement surface of the fixation structure 130 directly contacts the tissue of the native annulus.

The implant 100 can further include an extension member or brim 170. The extension member 170 can be an extension of the second sealing member 164, or it can be a separate component attached to the second sealing member 164 and/or the first portion 132 of the fixation structure 130. The extension member 170 can be a flexible member that, in a deployed state as shown in FIGS. 1A-1B, flexes relative to the first portion 132 of the fixation structure 130. In operation, the extension member 170 guides the implant 100 during implantation such that the device is located at a desired elevation and centered relative to the native annulus. In some embodiments, one or more components of the extension member 170 can be made of or include a radiopaque material.

As best shown in FIG. 1A, valve support 110 defines a first frame (e.g., an inner frame) and fixation structure 130 of the anchoring member 120 defines a second frame (e.g., an outer frame) that each include a plurality of structural elements. The fixation structure 130, more specifically, includes structural elements 137 arranged in diamond-shaped cells 138 that together form at least a substantially cylindrical ring when freely and fully expanded as shown in FIG. 1A. The structural elements 137 can be struts or other structural features formed from metal, polymers, or other suitable materials that can self-expand or be expanded by a balloon or other type of mechanical expander.

The fixation structure 130 can be a generally cylindrical fixation ring having an outwardly facing engagement surface. For example, in the example shown in FIG. 1A, the outer surfaces of the structural elements 137 define an annular engagement surface configured to press outwardly against the native annulus in the deployed state. In a fully expanded state without any restrictions, the fixation structure 130 is at least substantially parallel to the valve support 110. However, the fixation structure 130 can flex inwardly (arrow I) in the deployed state when it presses radially outwardly against the inner surface of the native annulus of a heart valve.

The first sealing member 162 lines the interior surface of the valve support 110, and the second sealing member 164 along the inner surface of the fixation structure 130. The extension member 170 has a flexible web 172 (e.g., a fabric) and a support member 174 (e.g., metal or polymeric strands) attached to the flexible web 172. The flexible web 172 can extend from the second sealing member 164 without a metal-to-metal connection between the fixation structure 130 and the support member 174. For example, the extension member 170 can be a continuation of the material of the second sealing member 164. Several embodiments of the extension member 170 are thus a floppy, resilient structure that can readily flex with respect to the fixation structure 130. The support member 174 can have a variety of configurations and be made from a variety of materials, such as a double-serpentine structure made from Nitinol. Additional details regarding the implant 100 can be found in U.S. patent Ser. No. 15/643,011, the disclosure of which is hereby incorporated by reference.

In one example, the implant 100 is a prosthetic tricuspid heart valve having a 48 mm diameter in the expanded arrangement and a length of 30.5 mm when compressed within a capsule having a 29 Fr outer diameter. In yet another example, the implant 100 is a prosthetic tricuspid valve implant having a 54 mm diameter in the expanded arrangement and a length of 34.3 mm when compressed within a capsule having a 29 Fr outer diameter.

Figure 2:
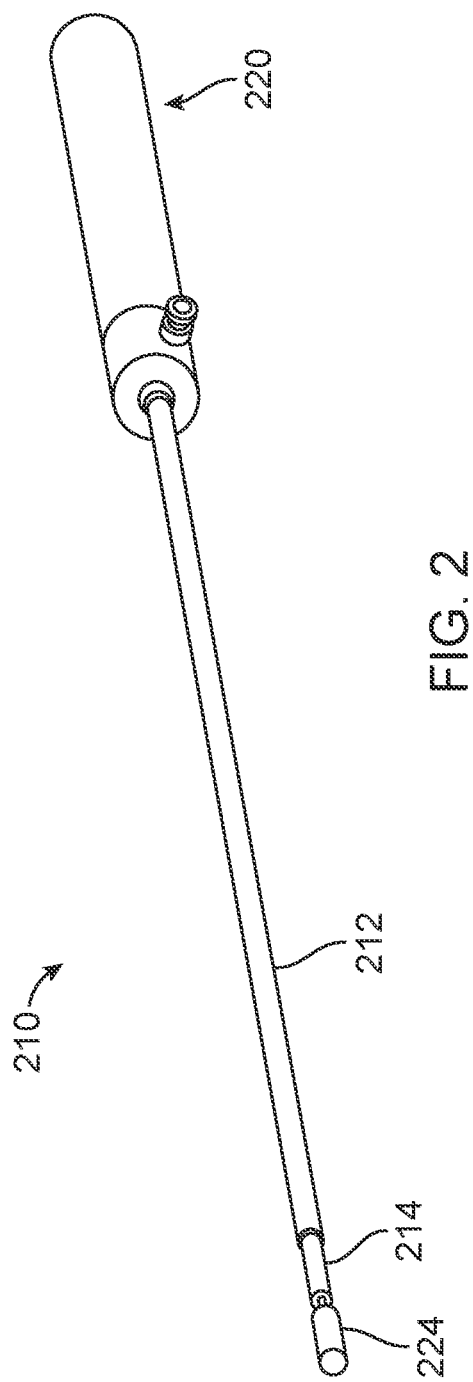
FIG. 2 is a perspective view of a delivery device suitable for delivering the prosthetic heart valve of FIGS. 1A-1C.
Figure 3:
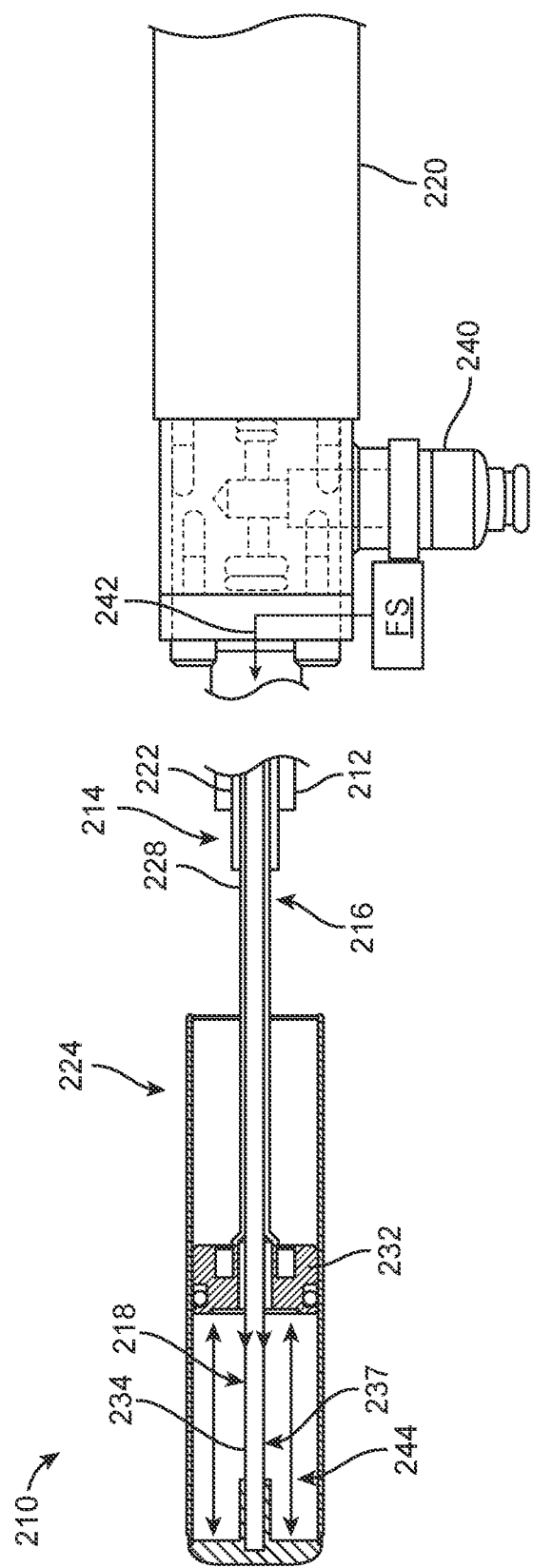
FIG. 3 is a schematic, cross-sectional illustration of select components of the delivery device of FIG. 2.

By way of background, a delivery device 210 for transcatheter delivery of an implant of the disclosure, such as the implant 100 of FIGS. 1A-1C is collectively shown in FIGS. 2-3. The delivery device 210 is useful with aspects of the disclosure. In general terms, the delivery device 210 is arranged and configured for percutaneously delivering a stented prosthetic heart valve 100 or other implant or prosthesis to a patient's native defective heart valve (see also FIGS. 1A-1C). Generally, the delivery device 210 includes an outer sheath 212, first catheter assembly 214, a second catheter assembly 216, a third catheter assembly 218 and a handle assembly 220. The second catheter assembly 216 includes a catheter 228 that supports a piston/valve retainer 232. The piston/valve retainer 232 can be of any type known in the art for releasably maintaining a prosthesis or implant on a delivery device for transcatheter delivery. The second catheter assembly 216 is positioned within the first catheter assembly 214. The third catheter assembly 218 includes a catheter 234 having a distal end 237 that supports a capsule assembly 224. The catheter 234 may optionally be hollow for defining a hydraulic fluid path, for example. The delivery device 210 provides a loaded, compressed arrangement in which the prosthetic valve 100 is loaded onto the catheter assembly 216 and is compressively retained on the piston/valve retainer 232 and entirely within the capsule assembly 224. Once loaded and compressed, the prosthetic valve 100 is located at a target site, the implant 100 is unsheathed from the capsule assembly 224 and is released from the piston/valve retainer 232 to permit the prosthetic valve 100 to self-expand to an expanded arrangement as shown in FIG. 1A. Movement of components 212, 214, 216 and 218, among others, can be actuated with the handle assembly 220. In one example, movement of one or more components is achieved with hydraulics. In such an example, the handle assembly 220 can be connected to a fluid source FS (FIG. 3) at port 240. Optionally, the fluid source FS may be fluidly connected to a fluid path 242 extending through the second catheter assembly 228 to a cavity 244 in the capsule assembly 224 to actuate movement of the capsule assembly 224 to free the implant, allowing the implant to release from the piston/valve retainer 232, fully deploying the implant.

Referring now in addition to FIGS. 4A-5B, which illustrate select components that can be incorporated into a delivery device 310, such as the delivery device 210 of FIGS. 2-3, for example. As at least partially indicated with like reference numbers, the delivery device 310 can be identically arranged and operated in a similar manner as compared to the delivery device 210 except as explicitly stated. In this embodiment, the delivery device 310 includes a telescoping capsule assembly 324 slidably secured to a distal end 337 of a catheter 334 of catheter assembly 318 with piston 331 having a bumper 332. The bumper 332 is a flexible disc with an atraumatic geometry such as tapered or rounded shape that helps with withdrawing the capsule assembly 324 through the deployed implant (e.g., implant 100) without snagging on the prosthetic leaflets. When the implant is crimped onto the catheter 334, the bumper 332 is compressed underneath the implant. When the implant is deployed, the bumper naturally expands and covers the proximal-most edge of the capsule assembly 324. The catheter 334 and bumper 332 can generally replace catheter 234 and piston/valve retainer 232 of the embodiment of FIG. 2-3. In one example, the capsule assembly 324 includes a proximal capsule 326 connected to a distal capsule 336 in both loaded and deployed arrangements. In this example, the proximal capsule 326 is configured to move distally over the distal capsule 336 in a telescoping fashion to deploy an implant compressively retained within the capsule assembly 324 (e.g., implant 100 or the like). Generally, the proximal capsule 326 has a larger inner diameter than an outer diameter of the distal capsule 336 so that the distal capsule 336 can nest within the proximal capsule 326. In one example, the distal capsule 336 is sized 29 French and the proximal capsule 326 is sized 35 French. In the loaded arrangement of FIG. 4A, the proximal capsule 326 and distal capsule 336 collectively fully sheathe and maintain the implant (e.g., implant 100; not shown in FIG. 4A for ease of illustration) in the compressed arrangement.

Figure 4A:
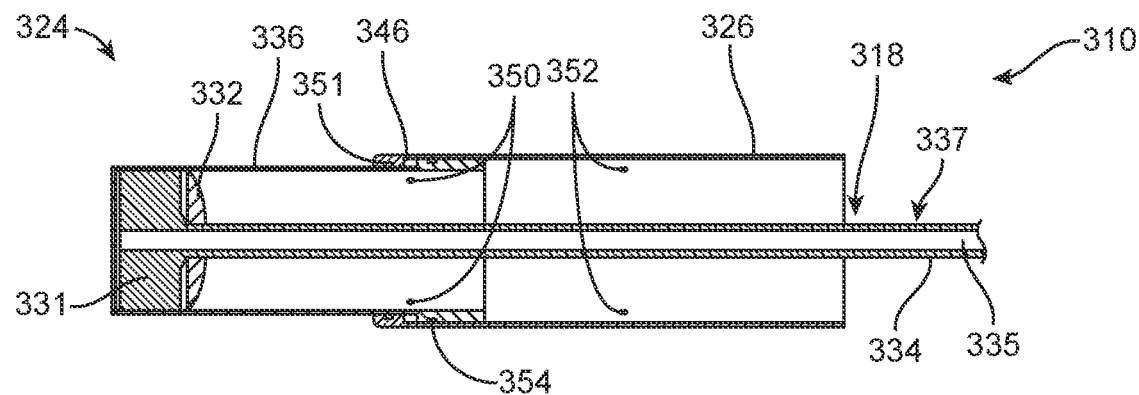
FIG. 4A is a schematic, cross-sectional illustration of a capsule assembly that can be utilized with the delivery device of FIGS. 2-3.
Figure 4B:
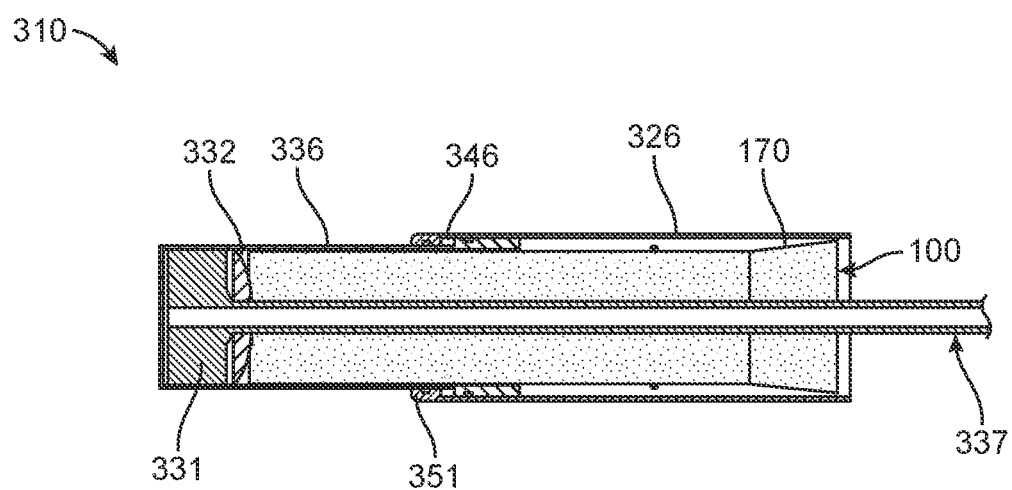
FIGS. 4B-4D are a schematic, cross-sectional illustrations of the capsule assembly of FIG. 4A having a distal capsule connected to a proximal capsule in a telescoping fashion, the capsule assembly sheathing a portion of an implant in a partially-deployed state having the implant released from the capsule assembly.
Figure 4C:
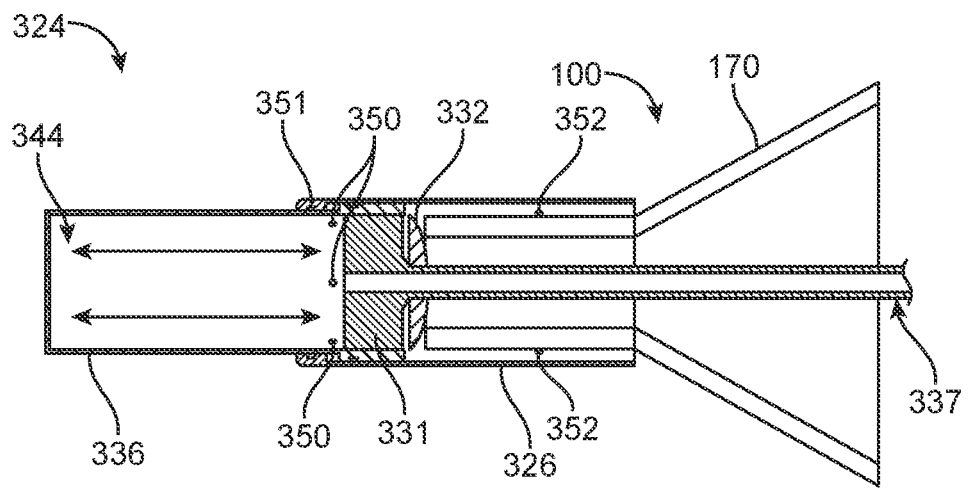
Figure 4D:
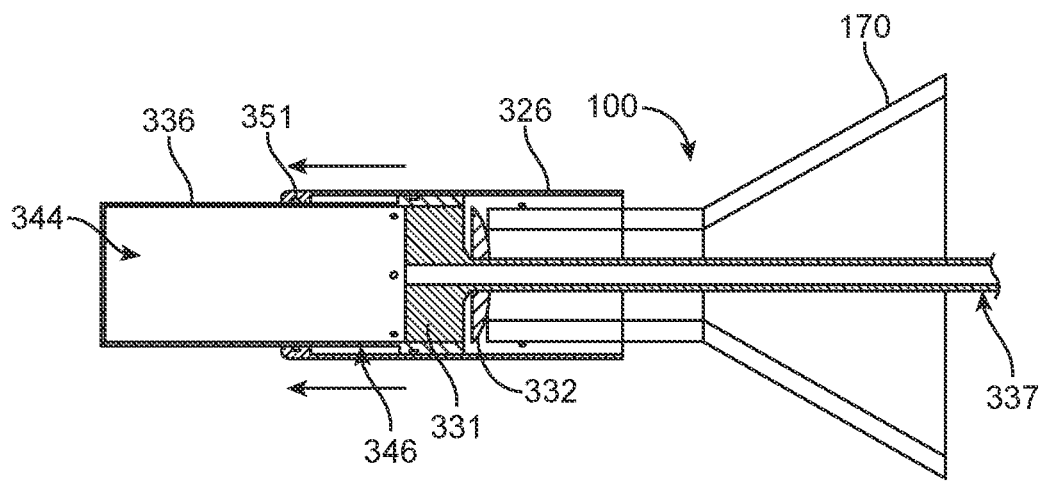
Figure 4E:
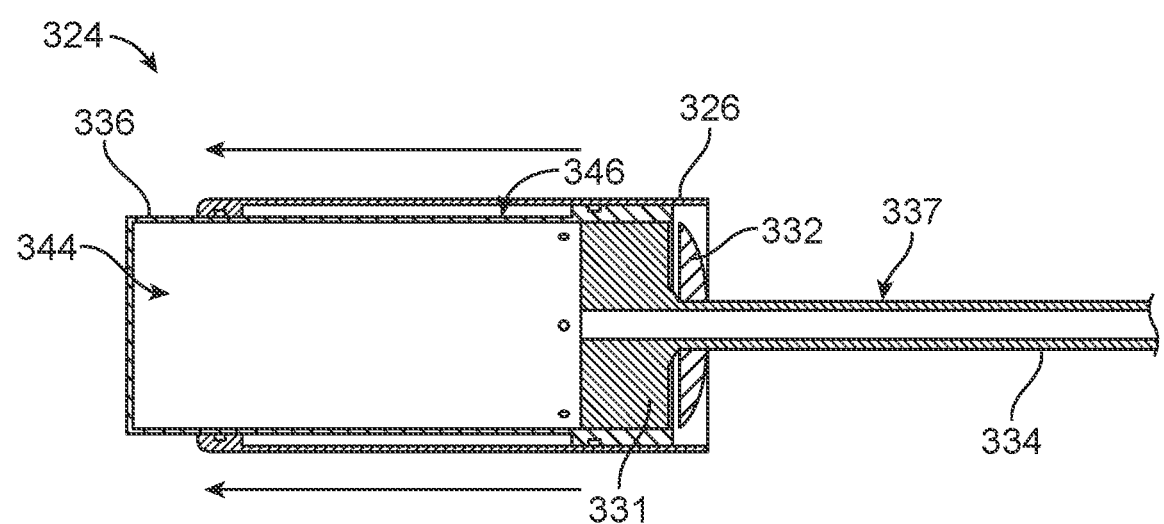
FIG. 4E is a schematic, cross-sectional illustration of the capsule assembly of FIGS. 4A-4D in a deployed state.
Figure 5A:
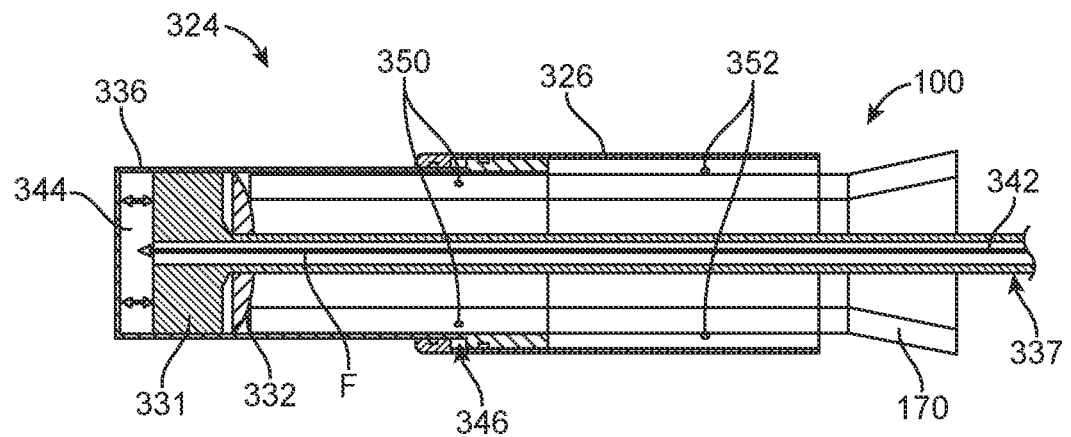
FIGS. 5A-5B are schematic cross-sectional views of the capsule assembly of FIG. 4A-4E illustrating part of a fluid deployment path suitable for transitioning the capsule assembly between a loaded arrangement to the partially-deployed and deployed arrangements.
Figure 5B:
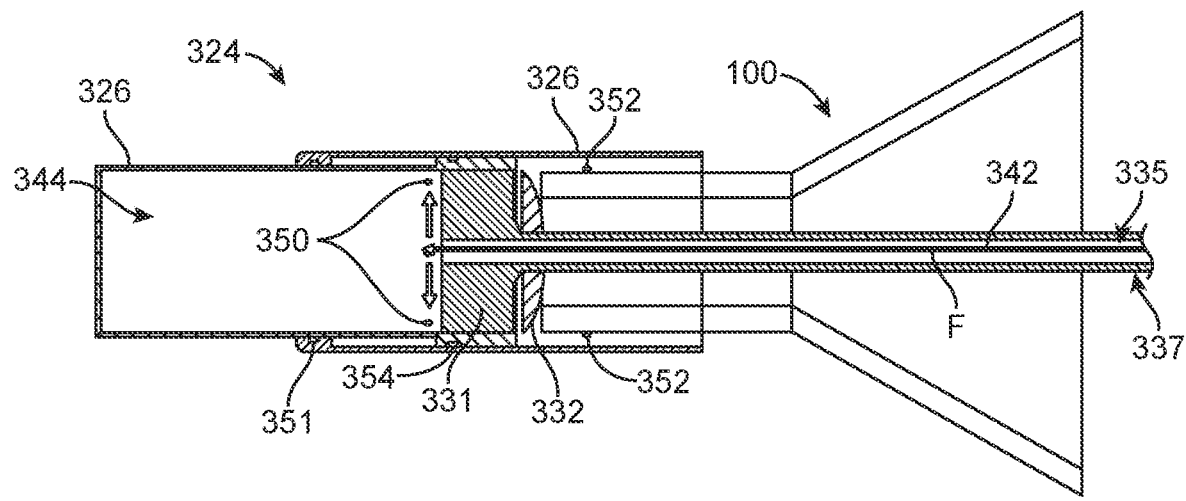

As shown in FIGS. 4B-4D, to unsheathe the prosthetic valve 100, actuation of the capsule assembly 324 to collapse the proximal capsule 326 and distal capsule 336 to unsheathe the implant can be achieved with hydraulics. As perhaps best shown in FIGS. 5A-5B the catheter 334 defines a lumen 335 forming fluid path 342 that can optionally extend to the fluid port 240 at the handle assembly 220 (see also, FIG. 3) for connection to the fluid source FS. In one example, the distal capsule 336 contains vent ports 350 and proximal capsule 326 contains vent ports 352. Vent ports 350 allow fluid transfer from cavity 344, formed by the distal capsule 336 and the piston 331, to the cavity 346, the space between distal capsule 336 and proximal capsule 326. Vent ports 352 connect a cavity 346 to the external environment. When hydraulic pressure is applied to cavity 344, the capsule assembly 324 is driven distally until vent ports 350 pass sealing member 351 (e.g., O-ring or the like), at which point hydraulic pressure may be vented or transmitted to cavity 346. Similarly, when hydraulic pressure is applied to cavity 346, the proximal capsule assembly 326 is driven distally until vent ports 352 pass sealing member 354, at which point hydraulic pressure may be vented or transmitted to the external environment. Fluid transfer to a cavity 344 at a distal end of both of the inner shaft and distal capsule 336 is transferred through vent port 350 and into cavity 346, which pushes the proximal capsule 326 over the distal capsule 336 to collapse the capsule assembly 324 in a telescoping manner (i.e. distally advance the proximal capsule 326). In the first phase when pressure is acting on cavity 344, both of the proximal and distal capsules 326, 336 move together distally to partially unsheathe the implant. As additional fluid is transferred into the cavity 346, the proximal capsule 326 slides over the distal capsule 336 to collapse and reduce a length L of the capsule assembly 324, while further unsheathing the implant. In one example, the length L in the loaded arrangement of FIG. 4A is 40 mm and the length of the capsule assembly 324 in the deployed arrangement of FIG. 4E is 26 mm. The deployed arrangement length indicates the length of the capsule assembly 324 that will enter the right ventricle in tricuspid valve replacement procedures (i.e. the distance of sub-annular travel). It is noted that this length of 26 mm is significant shorter than known devices.

The vent ports 350 of the distal capsule 336 also prevent the distal capsule 336 from extending proximally past the piston 331. The vent ports 352 serve a similar purpose and ensure that the proximal capsule 326 does not extend past the distal capsule 336. In one example, the device is configured such that the hydraulic force acting on the proximal capsule 326 is approximately 25% (+/−5%) of the hydraulic force acting on the distal capsule 336. O-rings 351, 354 or other seals can be used to form one or more fluid seals between the proximal capsule 326 and the distal capsule 336.

Figure 6:
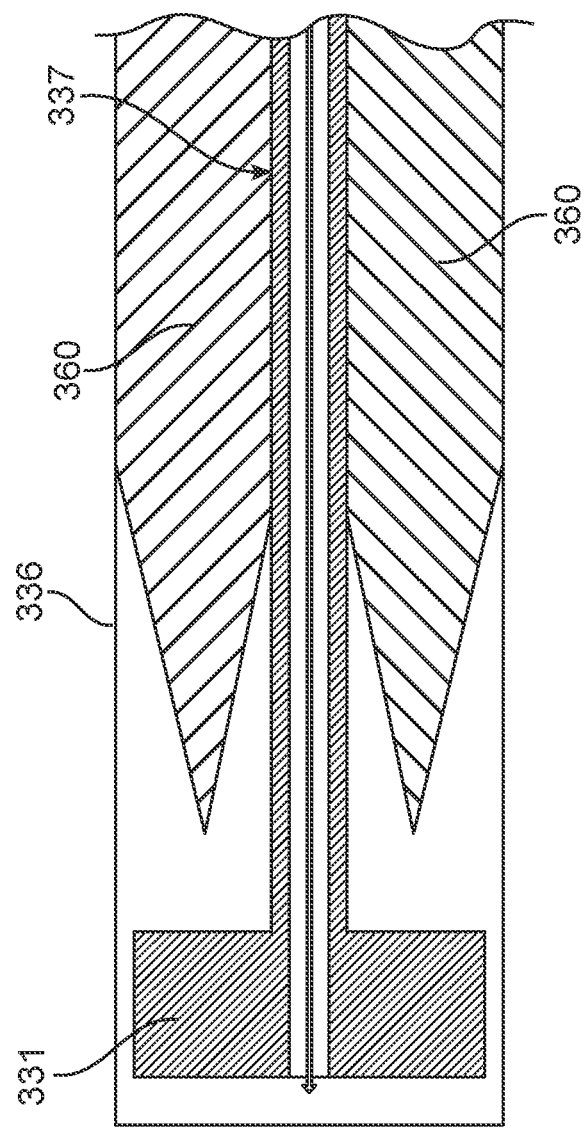
FIG. 6 is a partial, schematic cross-sectional illustration of the capsule assembly of FIGS. 4A-5B having the distal capsule optionally including an area having a higher coefficient of friction as compared to other areas of the distal capsule.

It is further envisioned that the friction between the distal capsule 336 and the proximal capsule 326 can be modified for various stages of implant deployment via surface treatments, seal material/design or providing a bearing material between the proximal and distal capsules 326, 336 or piston 331. For example, as schematically shown in FIG. 6, if a progressive force requirement was desired (i.e. a lower force required to initiate movement of the proximal capsule 326), at least a portion of an inner surface 360 of the distal capsule 336 can be modified to have a higher coefficient of friction as compared to the catheter 334. In one example, the portion of the inner surface 360 tapers in the distal direction. Other modifications are envisioned to provide a varying force required to transition the capsule assembly 324 from the loaded arrangement, to the partially-deployed arrangement to the deployed arrangement.

Figure 7:
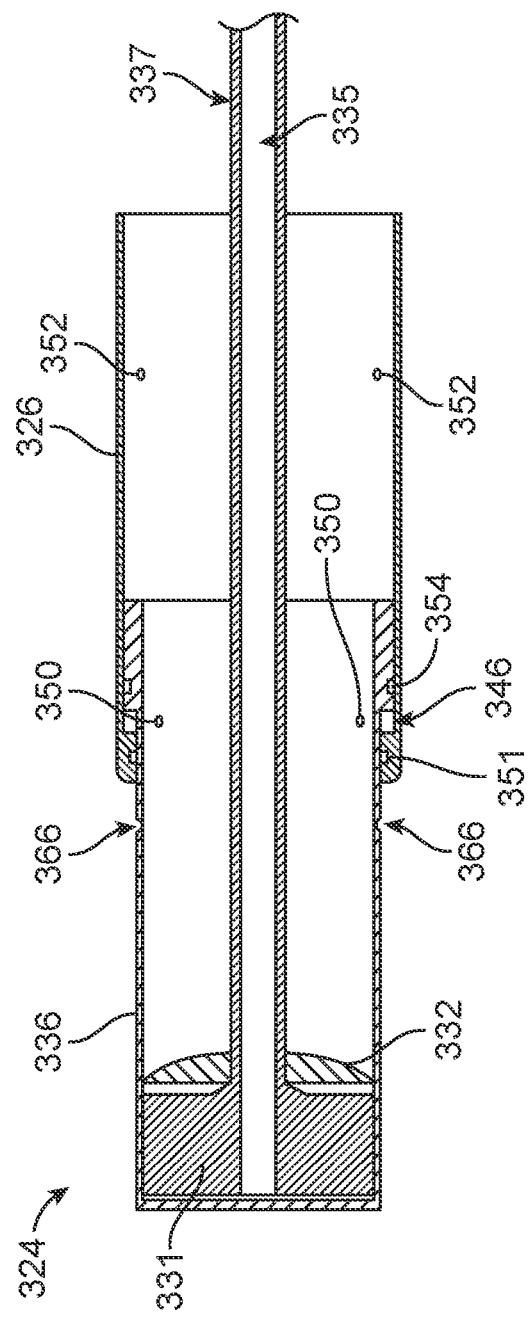
FIG. 7 is a schematic cross-sectional illustration of the capsule assembly of FIGS. 4A-5B including an optional annular detent.

Referring now in addition to FIG. 7, which illustrates the capsule assembly 324 of FIGS. 4A-4D modified to further include one or more detents 366 that provide resistance feedback during transition of the capsule assembly 324 from the loaded arrangement to the deployed arrangement. Any detents 366 in the outer surface of the distal capsule 336 create a region on the distal capsule 336 requiring higher force to distally advance the proximal capsule 326 therepast. A depth of each detent 366 may be limited by the ability of seal 351 (e.g., O-ring) to expand and maintain adequate sealing. Multiple detents 366 could be placed along a length of the distal capsule 336 as desired. The selected placement of the detents 366 can optionally be driven by implant design and the relevant stages of deployment for that specific implant to provide feedback for. Each detent 366 can be an annular groove or can be otherwise configured.

Figure 8A:
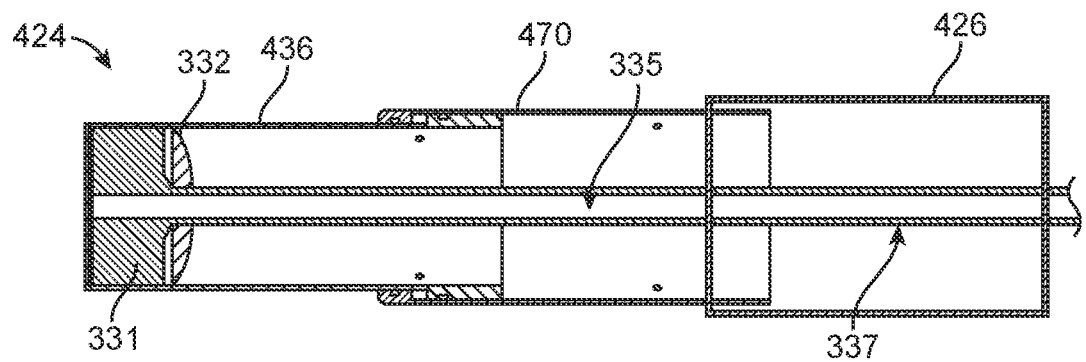
FIGS. 8A-8B are a schematic, cross-sectional illustrations of an alternate capsule assembly including a distal capsule, intermediate capsule and a proximal capsule.
Figure 8B:
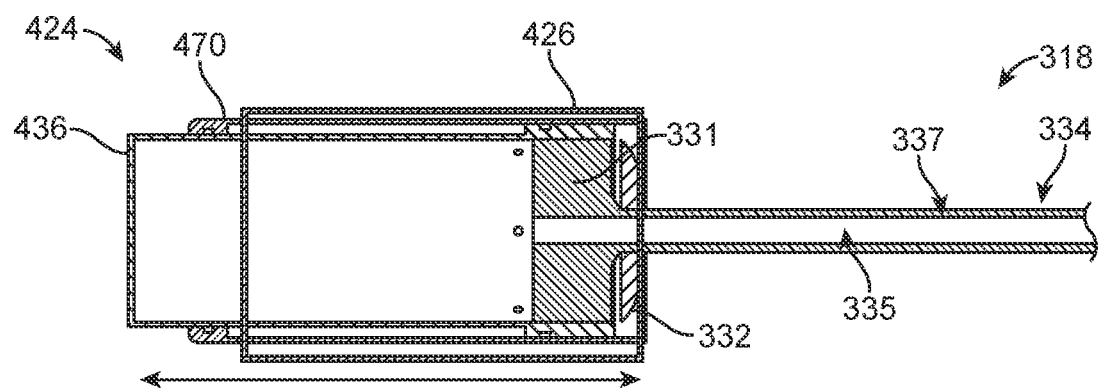

Referring now in addition to FIGS. 8A-8B, which schematically illustrate an alternate capsule assembly 424 that is identical in configuration and use to that of FIGS. 4A-6 except as explicitly stated. As indcted with like reference numbers, the capsule assembly 424 can be incorporated into delivery devices of the disclosure, including attachment to catheter assembly 318, which can be incorporated into the delivery device 210. In this embodiment, the capsule assembly 424 includes a proximal capsule 426, a distal capsule 436 and an intermediate capsule 470 assembled in a telescoping arrangement. In one example, the distal capsule 436 nests within the intermediate capsule 470, which nests with the proximal capsule 426. Therefore, the proximal portion 426 has a larger outer diameter than the intermediate capsule 470 and the distal capsule 436. Both the intermediate capsule 470 and proximal capsule 426 are proximal to the distal capsule 436 in the loaded arrangement (FIG. 8A) and translate distally to collapse the capsule assembly 424 over the distal capsule 436 in the deployed arrangement of FIG. 8B. In one example, the capsule assembly 424 has a length L' of 26 mm in the deployed arrangement. In such examples, one or more detents can be provided on an outer surface of one or more intermediate or distal capsules 470, 436, as desired, in the same manner described above with respect to FIG. 7. The capsule assembly 424 can included any of the features of delivery devices disclosed herein and can be operated in a similar manner as compared to any of the delivery devices or capsules disclosed herein to sheathe and deploy an implant contained within the capsule assembly 424. It will be further understood that one or more intermediate capsules 470 and the schematically shown proximal capsule 426 can be configured in a similar manner to the proximal capsules disclosed herein and can include vent ports, seals and cavities for receipt of fluid from the fluid path in a manner similar to that of FIGS. 5A-5B, for example.

The capsule assemblies disclosed herein are particularly beneficial for transcatheter tricuspid repair as various delivery devices are configured to reduce the depth in which the device needs to be inserted into the right ventricle during delivery of the prosthesis or the like. In one example, the capsule assembly has a length of 40 mm in the loaded arrangement for delivery and a length of 26 mm in the deployed arrangement for deploying the implant. Access to a tricuspid valve can be challenging in that existing implanted devices may be in the anatomy, reducing the space available for the delivery device. Further, chordae and papillary muscles serve as obstacles for delivery and the right ventricle is generally shorter than the left ventricle. All of these considerations result in a general desire for a delivery device capable of delivering an implant to a tricuspid valve while reducing a length the delivery device extends into the right ventricle.

Figure 9:
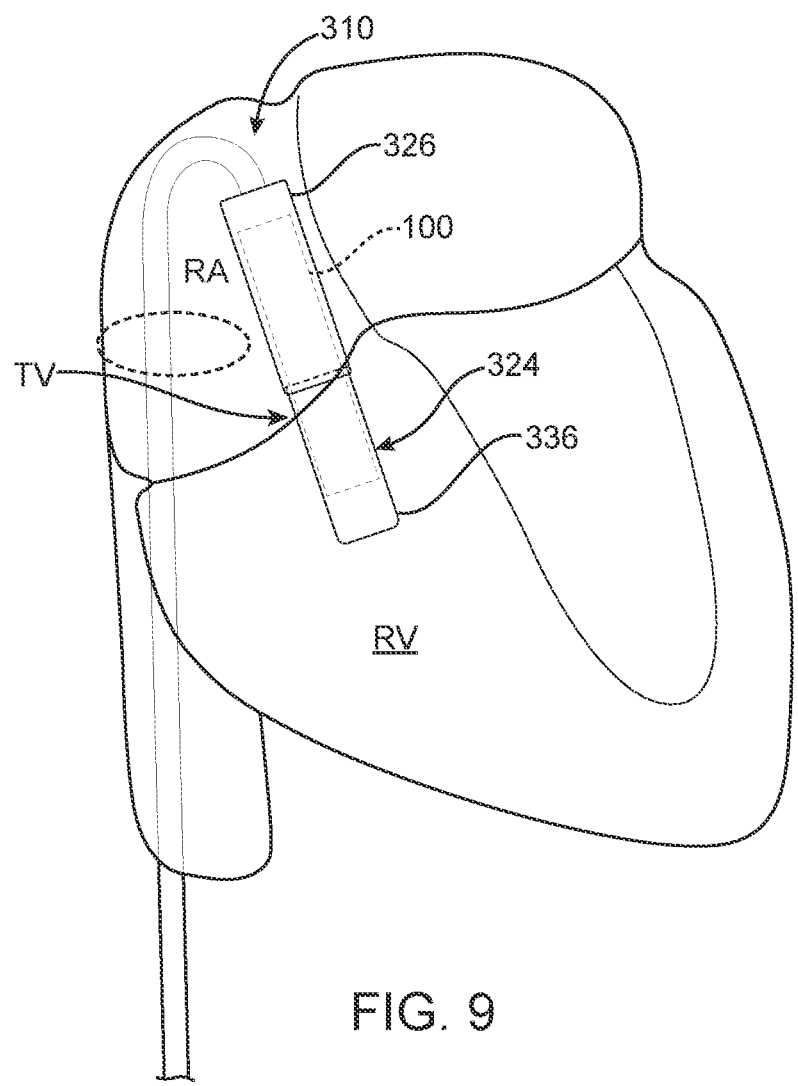
FIG. 9 is a schematic illustration of a method of the disclosure.

The present disclosure further includes methods of delivering an implant or other prosthesis disclosed herein to a heart valve utilizing devices of the disclosure. In one non-limiting example schematically depicted in FIG. 9, the heart valve is a tricuspid valve TV. Such methods can include providing the delivery device 310 including the capsule assembly 324 secured to catheter 234 (see also FIG. 4A). The distal capsule 336 is positioned distally with respect to the proximal capsule 326 in the loaded arrangement in which implant 100 is fully sheathed by the capsule assembly 324 and is positioned on the shaft 237. The method includes directing the delivery device 310 to the heart valve TV and transitioning the capsule assembly 324 from the loaded arrangement to an arrangement in which the proximal capsule 326 is advanced over the distal capsule 336 so that the proximal end or brim 170 of the implant 100 is at least partly unsheathed. In this step, the length L of the capsule assembly 324 is reduced. In one example, the delivery device 310 is delivered to the tricuspid valve TV and the distal capsule 336 is advanced through the valve annulus into the right ventricle RV and the capsule assembly 324 transitions to the partially-deployed state while the proximal capsule 326 is entirely in or at least partially in the right atrium RA. In some situations, a clinician may determine that after partial-deployment of the implant 100, repositioning of the implant is desired. In such situations the method can include proximally translating the proximal capsule 326 in a proximal direction over the implant 100 to lengthen the capsule assembly 324 and re-sheathe or recapture the implant for repositioning. Once the implant 100 is in the desired position, the capsule assembly 324 can be transitioned to the deployed arrangement, which includes reducing the length L of the capsule assembly 324 in a telescoping manner until the implant 100 is fully unsheathed and released from the capsule assembly 324.

With various telescoping capsule assemblies of the present disclosure, the delivery device extends a shorter distance into the right ventricle. In embodiments having one or more intermediate capsules, the intermediate capsules are distally advanced in a telescoping arrangement in the partially-deployed and deployed arrangements. Methods of valve replacement for other heart valves, such as a mitral valve, can be similarly conducted via differing delivery paths to access the heart valve to be or other cardiac structure in which the implant is to be delivered.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A cardiac implant delivery device comprising:
   a catheter assembly including a catheter having a distal end; and
   a capsule assembly secured to the distal end, the capsule assembly configured to sheathe the cardiac implant, the capsule assembly including a distal capsule and a proximal capsule, the distal capsule positioned distally with respect to the proximal capsule;
   wherein the capsule assembly includes a loaded arrangement, a partially deployed arrangement, and a deployed arrangement,
   wherein in the loaded arrangement, a distal end of the proximal capsule is adjacent a proximal end of the distal capsule,
   wherein in the partially deployed arrangement, the distal capsule and the proximal capsule are both translated distally as compared to the loaded arrangement, and
   wherein in the deployed arrangement, the proximal capsule is translated distally with respect to the distal capsule as compared to the partially deployed arrangement.

2. The delivery device of claim 1, wherein a cavity for receiving fluid is formed between the distal capsule and the proximal capsule.

3. The delivery device of claim 2, wherein the distal capsule includes radially extending vent ports to direct fluid from within the distal capsule to the cavity.

4. The delivery device of claim 1, wherein the cardiac implant is a stented prosthesis, the delivery device further comprising the stented prosthesis positioned onto the distal end of the catheter and covered by both of the distal capsule and the proximal capsule in the loaded arrangement.

5. The delivery device of claim 1, wherein the proximal capsule is positioned at least partially over the distal capsule in the loaded arrangement, in the partially deployed arrangement, and in the deployed arrangement.

6. The delivery device of claim 1, wherein the capsule assembly includes an intermediate capsule positioned between the distal capsule and the proximal capsule in the loaded arrangement; wherein the intermediate capsule moves distally over the distal capsule in the deployed arrangement.

7. The delivery device of claim 1, wherein an inner surface of the distal capsule has an increased coefficient of friction as compared to the distal end of the catheter.

8. The delivery device of claim 1, wherein an outer surface of the distal capsule includes a detent.

9. The delivery device of claim 1, wherein:
the distal capsule defines a first cavity for receiving fluid, wherein in the partially deployed arrangement the first cavity is filled with fluid;
a second cavity is defined between an outer surface of the distal capsule and an inner surface of the proximal capsule, wherein in the deployed arrangement the second cavity is filled with fluid; and
first vent ports extending radially through the distal capsule such that in the partially deployed arrangement the first vent ports are aligned with the second cavity to enable fluid flow from the first cavity to the second cavity.

10. The delivery device of claim 9, wherein the proximal capsule includes second vent ports extending radially therethrough, wherein in the deployed arrangement the second vent ports are aligned with the second cavity to enable fluid flow from the second cavity to outside the capsule assembly.

11. A method of delivering an implant to a heart valve, the method comprising:
directing a delivery device to the heart valve, the delivery device including:
a catheter assembly including a catheter having a distal end; and
a capsule assembly secured to the distal end; the capsule assembly configured to sheathe the implant, the capsule assembly including a distal capsule and a proximal capsule, the distal capsule positioned distally with respect to the proximal capsule in a loaded arrangement, wherein the implant is secured over the distal end and within the capsule assembly;
transitioning the capsule assembly from the loaded arrangement to a partially deployed arrangement by advancing both the distal capsule and the proximal capsule distally; and
transitioning the capsule assembly from the partially deployed arrangement to a deployed arrangement by advancing the proximal capsule distally over the distal capsule.

12. The method of claim 11, further comprising proximally withdrawing the proximal capsule to re-sheathe and reposition the implant.

13. The method of claim 11, wherein the capsule assembly includes an intermediate capsule positioned between the distal capsule and the proximal capsule in the loaded arrangement, wherein the intermediate capsule moves distally over the distal capsule as the capsule assembly transitions to the deployed arrangement.

14. The method of claim 11, wherein the heart valve is a tricuspid valve.

15. The method of claim 14, wherein the capsule assembly is delivered from a right atrium to the tricuspid valve, wherein the step of transitioning the capsule assembly from the loaded arrangement to the partially-deployed arrangement begins with the proximal capsule within the right atrium.

16. The method of claim 11, wherein advancing both the proximal capsule and the distal capsule distally includes directing fluid into a first cavity formed in the distal capsule.

17. The method of claim 16, wherein advancing the proximal capsule distally over the distal capsule comprises directing fluid into a second cavity formed between the distal capsule and the proximal capsule.

* * * * *